United States Patent
Yarnitsky

(10) Patent No.: US 8,774,925 B2
(45) Date of Patent: Jul. 8, 2014

(54) PAIN MODULATION SYSTEMS AND METHODS

(76) Inventor: David Yarnitsky, Haifa (IL)

( * ) Notice: Subject to any disclaimer, the term of this patent is extended or adjusted under 35 U.S.C. 154(b) by 0 days.

(21) Appl. No.: 13/377,557

(22) PCT Filed: Jun. 11, 2010

(86) PCT No.: PCT/IB2010/052619
§ 371 (c)(1),
(2), (4) Date: Dec. 11, 2011

(87) PCT Pub. No.: WO2010/143164
PCT Pub. Date: Dec. 16, 2010

(65) Prior Publication Data
US 2012/0083858 A1 Apr. 5, 2012

Related U.S. Application Data

(60) Provisional application No. 61/186,027, filed on Jun. 11, 2009.

(51) Int. Cl.
*A61N 1/34* (2006.01)
(52) U.S. Cl.
USPC .............................. 607/46; 607/62
(58) Field of Classification Search
USPC ..................... 600/300; 607/46, 62
See application file for complete search history.

(56) References Cited

U.S. PATENT DOCUMENTS

| | | | |
|---|---|---|---|
| 5,938,690 A * | 8/1999 | Law et al. | 607/46 |
| 6,522,927 B1 | 2/2003 | Bishay | |
| 7,006,859 B1 | 2/2006 | Osorio | |
| 7,155,287 B2 | 12/2006 | Gavronsky | |
| 7,200,444 B2 | 4/2007 | Gavronsky | |
| 2004/0087838 A1 | 5/2004 | Galloway | |
| 2008/0021505 A1 | 1/2008 | Hastings | |
| 2009/0192406 A1 | 7/2009 | Larsen | |
| 2010/0137939 A1 | 6/2010 | Liu | |
| 2010/0312166 A1 * | 12/2010 | Castel | 604/20 |

OTHER PUBLICATIONS

Granot, Michal, et al. "Determinants of endogenous analgesia magnitude in a diffuse noxious inhibitory control (DNIC) paradigm: Do conditioning stimulus painfulness, gender, and personality variables matter?". May 2008. The Journal of the International Association for the Study of Pain. vol. 136, p. 142-149.*
Electroacupuncture reduces Back Pain in Elderly Patients. Accupuncture Today, Aug. 2003 vol. 04, Iss 08.

* cited by examiner

*Primary Examiner* — Christopher D Koharski
*Assistant Examiner* — Michael Carey
(74) *Attorney, Agent, or Firm* — The IP Law Firm of Guy Levi, LLC; Guy Levi

(57) ABSTRACT

Systems and methods of conducing a conditioning modulation of pain perception are disclosed. The system includes a power source, an impulse generator, a controller and at least one electrode for the delivery of a therapeutic stimulation.

1 Claim, 3 Drawing Sheets

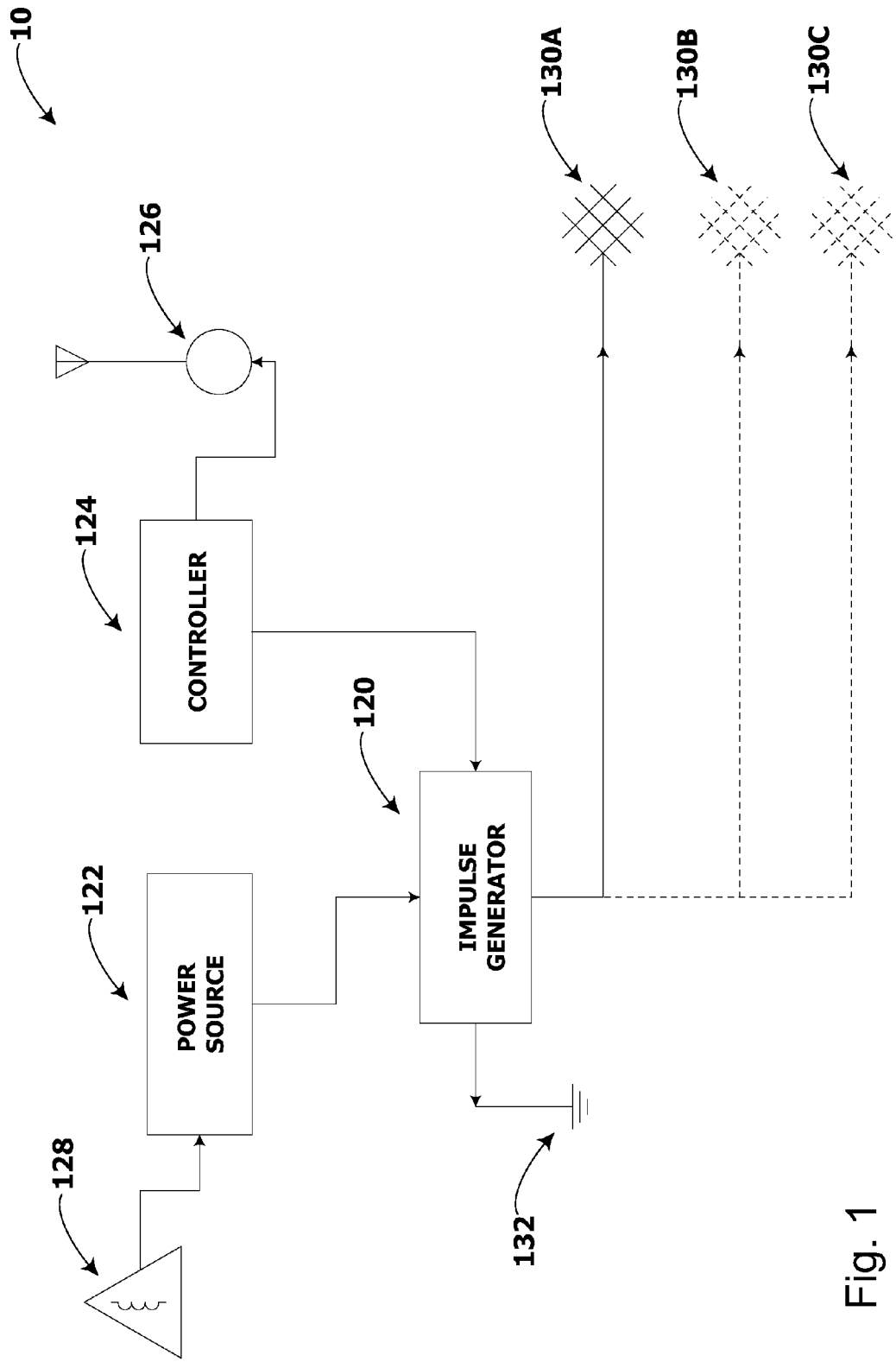

PAIN MODULATION SYSTEMS AND METHODS

CROSS-REFERENCE TO RELATED APPLICATIONS

This application is a U.S. National Phase Application under 35 U.S.C. 371 of PCT International Application No. PCT/IB2010/052619, which has an international filing date of Jun. 11, 2010, and which claims priority from U.S. Provisional Patent Application No. 61/186,027, filed Jun. 11, 2009, all of which disclosures are hereby incorporated by reference.

FIELD OF THE INVENTION

The present invention relates to therapeutic systems and methods in general. More particularly, the present invention relates to systems for modulating pain and a method for using same.

BACKGROUND OF THE INVENTION

Pain sensation is typically the result of peripherally generated neural stimuli, which are transmitted therefrom and modulated in the CNS before arriving in the cortex and in the consciousness. Tests for modulation mechanisms known in the art include the diffuse noxious inhibitory control (DNIC). Diffuse noxious inhibitory control (DNIC) represents the endogenous analgesia system, where modulatory effect is exerted on incoming spinal nociceptive neural stimuli. This phenomenon is based on a spinal-bulbar-spinal loop, under cerebral control, which, at least partially, is opioid-mediated. DNIC is typically tested in the lab using the 'pain inhibits pain' paradigm, by two remote noxious stimuli, the 'conditioning' pain on the one hand, and on the other hand an inhibiting one, the 'test' pain.

Pain summation is complex as two adjacent nociceptive stimuli cause an additive effect, whereas two remote nociceptive stimuli cause an inhibitory effect. Neuroanatomical distribution is associated with this process. Temporally-wise, a certain frequency makes a difference between summation and adaptation for a specific stimulus Therapy for neuropathic pain, despite newly presented drugs, is still frustrating, with less than half of the patients not achieving satisfactory relief; possibly due to the lack of mechanism-oriented choice of therapy. Currently, it is mainly the consideration of side effects which inspires the physician in choosing the anti-neuropathic pain medication, rather than, ideally, its mechanism of action. Several lines of pharmacological therapy are recommended for neuropathic pain; anti-depressants, antiepileptics and opioids.

Antidepressants include tricyclics and SNRIs (Serotonin and noradrenaline reuptake Inhibitor), since SSRIs (selective serotonin reuptake inhibitors) have proven less effective in treating neuropathic pain. Tricyclics have been the mainstay of therapy for many years, giving a fairly good number need to treat (NNT) of 2-3, but with considerable adverse effects especially in older patients (Watson et al., 1998). SNRIs such as the medicines commercialized under trademarks of Venlafaxine and Duloxetine which have proven as effective for neuropathic pain, mainly for diabetic neuropathy (Goldstein et al., 2005), with a slightly less favourable NNT (4-6), but more favourable side effect profile (Wernicke et al., 2007). The mechanism of action of both tricyclics and SNRIs is to increase synaptic levels of both serotonin (5-hdroxytryptamine or 5-HT) and noradrenaline (NA), via a dual inhibition of their reuptake in the CNS. An increased level of these neurotransmitters exerts descending modulation via the bulbo-spinal tracts, augmenting the inhibitory effect on pain perception. Of the antiepileptics, the medications that seem to be most relevant for neuropathic pain are gabapentin (GBP) and pregabalin (PGB) (Chandra et al., 2006), whereas the medicines commercialized under trademarks of oxcarbamazepine and lamotrigine showed lesser effects (Viniket al., 2007). PGB and GBP inhibit the presynaptic $\alpha$-2-$\delta$ subunit of the Ca channel, and are therefore expected to diminish effects that depend on calcium influx, including central sensitization. The role of opioids in neuropathic pain is still controversial; while convincing evidence has been accumulated in recent years for efficacy in neuropathic pain, the safety profile is still unclear, leading the recent EFNS guideline to recommend opioids as second line medications for neuropathic pain (Attal et al., 2006).

Accordingly, implementation of the DNIC phenomenon for assessing the pain modulation profile of a patient as well as for clinically beneficially modulating the pain sensation and to provide relief for pain-inflicted patients, in addition or as an alternative to the pharmaceutical treatment, is called for.

SUMMARY OF THE INVENTION

The present invention employs the endogenous analgesia system to achieve a Conditioned Pain Modulation (hereinafter CPM). The perception of pain is modulated by affecting the diffuse noxious inhibitory control (DNIC); thereby achieving the CPM of aforesaid perception. DNIC is preferably affected by an electrical stimulation.

BRIEF DESCRIPTION OF THE DRAWINGS

The present invention will be understood and appreciated more fully from the following detailed description taken in conjunction with the appended drawings in which:

FIG. 1 is a schematic diagram of an exemplary pain modulation system of the present invention;

DISCLOSURE OF THE INVENTION

Figure 2A:
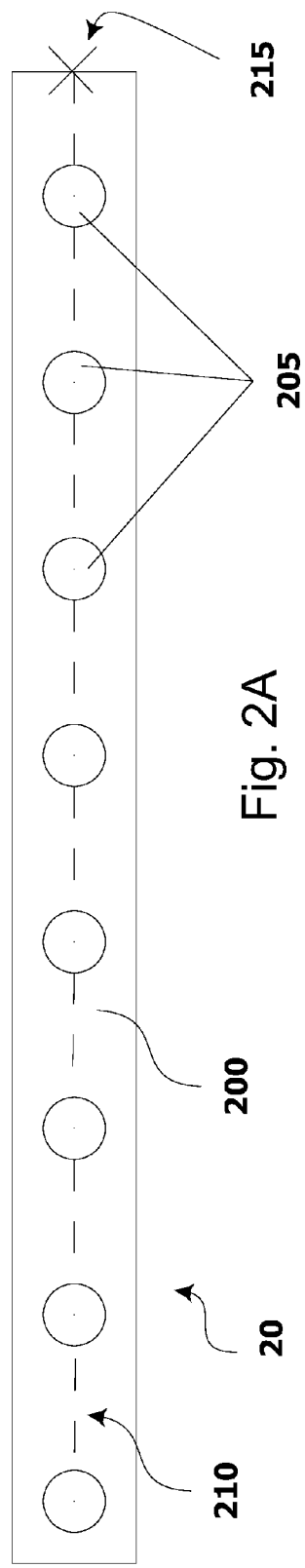
FIGS. 2A and 2B are schematic diagram of an exemplary multi-site electrodes in accordance with some preferred embodiments of the present invention.

Illustrative embodiments of the invention are described below. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which vary from one implementation to another. Moreover, it will be appreciated that such a development effort might be complex and time-consuming, but would nevertheless be a routine undertaking for those of ordinary skill in the art having the benefit of this disclosure.

In accordance with some preferable embodiments of the present invention, the CPM profile and/or subjective pain threshold level of a patient are/is initially evaluated, to assess the efficacy of a proposed treatment and/or determine the patient specific parameters which will yield the optimal therapeutic result. The CPM profile is inherently related to the individual characteristics of the DNIC pathway mechanism of the patient.

According to an exemplary testing procedure, the CPM profile is assessed as the difference of pain ratings to test stimulus (henceforth TS) applied before and during the immersion of the contralateral hand area into a hot water bath, providing a conditioning stimulus, (henceforth CS), as elaborated infra. Exemplary test stimulus (TS) of a 30 seconds period induced by a physical contact a heat element, such as 30×30 mm$^2$ thermode TSA-2001 available from Medoc. TS can be delivered to the non-dominant forearm at a predetermined temperature. The TS temperature can be raised from initial 32° C. by 2° C./sec to the destination temperature. The destination TS is preferably to evoke a pain sensation with an intensity of 60 on a 0-100 NPS scale (described in more details in Granot et al., 2006). Fifteen minutes after the completion the first pre-immersion test, the patient is asked to immerse his/her dominant hand for 1 min into a water bath at 46.5° C. (Heto Cooling Bath CBN 8-30, Allerod, Denmark). Thereafter second application of the test stimulus TS is repeated during last 30 seconds of immersion.

To assess the residual CPM effect, underlaid by patent's specific DNIC responsiveness, following the immersion test, the TS may be applied for a third time. During each application of the TS, the patient preferably rates his/her thermal pain intensity every 10 seconds (more details in Granot M, Weissmann Fogel I, Crispel Y, Granovsky Y, Yarnitsky D, Determinants of endogenous analgesia magnitude in a diffuse noxious inhibitory control (DNIC) paradigm: Do conditioning stimulus painfulness, gender and personality variables matter?. Pain 136, 142-9, 2008).

The subjective pain threshold level of a patient can be exemplarily assessed in a similar manner by a temperature stimulus that is raised by 2° C./sec from 32° C. or any other sub-threshold value to the destination temperature in which pain or another sensation is perceived by the patient.

Exemplarily, mechanically evoked stimuli can be assessed by contacting a subject with the 6.45 mN von Frey filament (Stoeteling Ltd. US).

A non-limiting list of means for evoking the conditioning stimuli includes water baths, a heating surface, a soft surface on which a patient puts an hand, and is subjected to either heating or cooling, a plurality of small surfaces in contact with the hand each heating or cooling, an array of electrodes that give electrical stimuli, optionally in a few places on the hand, a blood pressure cuff to be inflated for a short time, causing pain, a thermal glove or a glove like made of two surfaces that can be opened in-between two heating elements, optionally including a few sources over the hand, combination of two or more modalities of stimulation out of thermal, electrical, mechanical, chemical, etc.

The rating of the score tests is preferably carried out with reference to the numerical pain scale (NPS) described in the publications of Ayesh et al., 2007 and Baad-Hansen et al., 2003 and/or by brief pain inventory (BPI), as elaborated by Cleeland & Ryan, 1994. A plurality of repetitive tests may be performed on a subject to attain a reliable statistic significance of the scores.

Subsequently, the locations for applying the therapeutic stimulation for the CPM are selected. The locations for CPM stimulation are selected with a certain relation to the location of pain-inflicted area, as in instances of localized pain. The locations for CPM or may be selected arbitrarily in instances of non-localized or neuropathic/idiopathic pains and tested thereafter for efficacy. The locations are selected in accordance with the DNIC paradigm, e.g. locations that can conduce a more efficient inhibitory effect, and/or according to the expediency that may be detected during the application of the testing stimulation. The CPM stimulation is preferably to be applied to peripheral pain nerve fibers. The locations for applying the CPM stimulation are selected to preferably include several different dermatomes; thereby simultaneous application of the therapeutic stimulation to distinct spinal roots is achieved.

Preferably, the CPM stimulation is electrical and applied intracorporeally, in particular to the subcutaneous tissue. However the CPM stimulation in accordance with the present invention is not limited to the electrical subcutaneous stimulation and can be applied inter alia percutaneously. The CPM stimulation can be applied by either one of the techniques elaborated supra. If the electrical subcutaneous stimulation is implemented, the patient is implanted with a subcutaneous electrode by a minimally-invasive surgical procedure. The electrode is electrically connected to an impulse generator and electric impulses can thence be affected via the implanted electrode. The intensities of the electric impulses that do not exceed the subjective pain threshold level of the patient can thus be assessed/reassessed. The controller of the impulse generator is programmed to carry out a regimen of the therapeutic CPM stimulation, as will be elaborated infra.

Preferably, the CPM stimulation is performed using intensities of electric impulses that do not exceed the subjective pain threshold level of the patient. However, if a sub-threshold level stimulation fails to achieve a desired CPM effect, additionally or alternatively, stimulation at supra-threshold levels can be implemented.

Preferably, the therapeutic stimulation is performed during the night, while the patient asleep; thereby inducing an accumulatory post-effect that efficiently modulates patient's pain perception during the daytime, while the patient is awake.

Although the CPM stimulation in accordance with the present invention can be beneficially implemented to relieve a wide variety of pains, it is particularly beneficial for neuropathic/idiopathic pains.

An exemplary system for applying the CPM stimulation in accordance with some embodiments of the present invention is described next. First, reference is made to FIG. 1, in which system 10 is shown. If the intracorporeal stimulation is implemented, system 10 is preferably implanted into the patient. Some or all constituents of system 10 are typically enclosed in biocompatible casings. System 10 includes impulse generator 120 that is electrically connected to power source 122 and receives energy therefrom. Controller 124 is programmed to carry out a regime of the CPM stimulation, and is electrically connected to impulse generator 120, controlling the operation thereof. Controller 124 typically includes an internal clock (not shown) and is preferably associated with communication module 126. Communication module 126 preferably has an RF antenna for a wireless communication with an external programming module (not shown); thereby the regime of the therapeutic stimulation of controller 124 for impulse generator 120 can be updated/reprogrammed. Controller 124 further comprises a wireless communication module (not shown), for connection with a programmer unit. Power source 122 is preferably electrically connected to induction coil 128; thereby by electromagnetically inducing coil 128, for instance by another coil (not shown), power source 122 can be recharged.

Impulse generator 120 is further connected to at least one or preferably to a plurality of multi-site electrode/s 130 A-C. Optionally, impulse generator 120 is connected to common ground point 132; however in some embodiments the ground point is not a common one but rather each site of the multi-site electrode comprises a cathode-anode couple. Alternatively, a common ground serves several sites of the multi-site distributed electrode or each multi-site electrode has a common ground point; thus a plurality of ground points can be implemented.

Figure 2B:
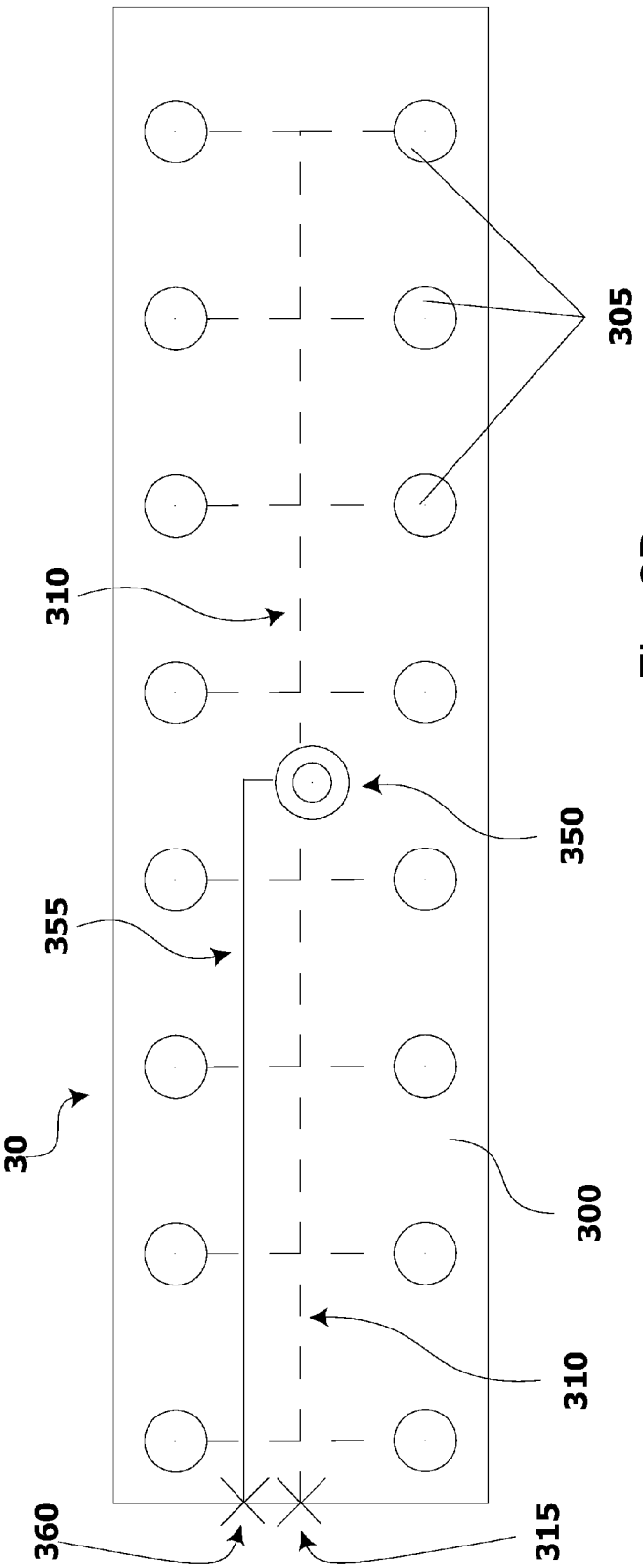

Reference is made to FIGS. 2A and 2B, in which exemplary distributed multi-site electrodes 20 and 30 are shown. Multi-site electrode 20 is formed by strip 200, typically made of an electrically nonconductive flexible material. A plurality of discreet sites 205, are preferably equidistantly disposed therein, along the centreline of strip 200. Each contact point 205 of distributed electrode 20 is exteriorly exposed to form electrical contact with exposed subtending tissues and to be capable to conduct an electrical current thereto; noticeably contact points 205 can be exposed to either side of strip 200 or preferably to both sides. Preferably embedded conduit 210 electrically connects contact points 205 to connector port 215, which can be connected, typically by a cable (not shown), to the impulse generator of the system of the present invention (not shown). The return ground point for contact points 205 can be, for instance, an electrically conductive casing of the impulse generator and/or some other constituents of the system of the present invention.

Multi-site electrode 30 is formed by band 300, typically made of electrically nonconductive flexible material. A plurality of discreet contact points 305, preferably arranged in grid, is disposed therein. Each contact point 305 is exteriorly exposed to form electrical contact with adjacently laying tissues and to be capable to conduct an electrical current thereto; noticeably the sites 305 can be exteriorly exposed facing to either side of strip 300 or preferably to both sides. Preferably embedded multifurcating conduit 310 electrically connects contact points 305 to connector port 315, which can be connected, typically by a cable, to the impulse generator of the system of the present invention (not shown). Multi-site electrode 30 incorporates common ground pad 350 electrically connected to connector port 360, which together with port 315 can form a joint connector unit that can be connected to the impulse generator of the system of the present invention. In some embodiments the common ground pad is a strip of electrically conductive material disposed along the centreline of band 300, exteriorly exposed facing to either side of strip 300 or preferably to both sides.

APPLICATION OF THE INVENTION

Applications of the therapeutic method and/or system of the present invention are, inter alia, indicated for idiopathic and neuropathic pains. These include diabetic neuropathy, uremic neuropathy, post herpetic neuralgia, post operative neuropathic pain, low back pains, traumatic nerve lesions usually to the limbs, neuropathy due to chemotherapy which is known to be caused by vincristine, taxol, platinot, thalidomide and a few additional new chemo agents can cause pain neuropathy, hereditary neuropathy, pesticide induced neuropathy and post-operative pains. Idiopathic pains as referred herein, inter alia, in particular include pains inflicted by syndromes such as: fibromyalgia, temporomandibular diorders, irritable bowel syndrome, tension type headache, atypical facial pain, migraine, vulvar vestibulitis and low back pains.

It should be stressed however that the applications of the therapeutic method and/or system of the present invention are not limited by an indication to any particular pain, since the therapeutic method and/or system of the present invention are clinically beneficial virtually for any pain that can be experienced by a patient.

Example

Experimental Setup

Two applications testing DNIC were performed. Firstly, the TS was applied solitarily, with no additional stimuli, hereafter referred to as baseline TS. Twenty minutes thereafter delivering the baseline TS, an identical stimulation was applied for the second time simultaneously with a CS, either noxious or non-noxious. The difference between the scores of the TS applications was taken as the CPM value.

Test Stimuli

The intensity of the TS was determined for 28 healthy volunteers, enrolled in a clinical study, as the temperature that induced a pain experience at a magnitude of 60 on a 0-100 NPS (for further details, see Granot et al., 2008). In order to avoid possible residual effects induced by a previous effects, an at least 15 minutes interval was kept before the onset of the conditioning stimuli protocol.

The duration of the TS was 30 seconds. During the test stimulation, subjects rated the level of pain intensity three times: at 10, 20, and 30 sec after its initiation. The TS was applied solitarily (as baseline test stimulation, fifteen minutes after the determination of the test-pain intensity.

Conditioning Stimuli

The CS was a non-dominant hand hot water immersion for 60 seconds in a still position with the fingers wide apart. The hot water was used at temperatures of 44.5° and 46.5° C., which were randomly delivered in separate tests. In order to avoid bias of residual effects induced by a previous noxious stimulus, 20-minute breaks were kept between the different applications of CS.

Figure 3:
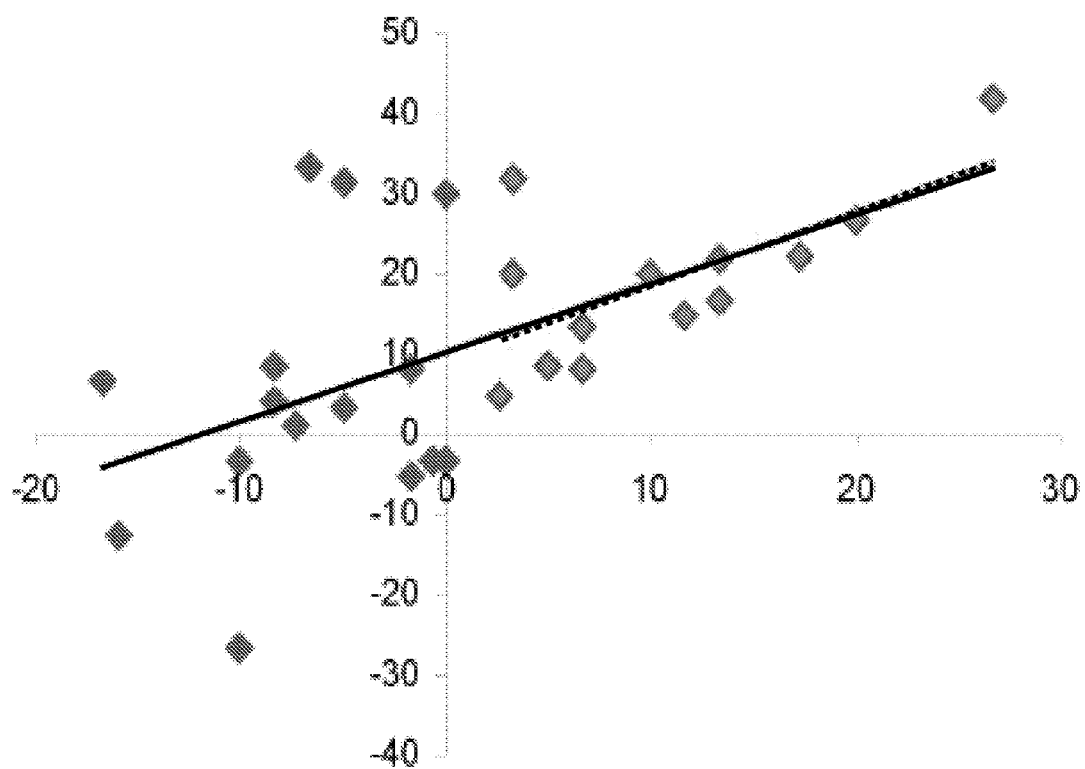
FIG. 3 is a plot of empirical results that were obtained in a clinical study.

Reference is now made to FIG. 3, which is a plot of empirical results obtained according to the above-identified protocol, wherein the X-axis is the CPM value observed for a painful CS of 46.5° C.; whereas the Y-axis is the CPM value observed for a CS of 44.5° C. All subjects represented by the points above the X-axis are characterized by a positive CPM value for a painful CS. CPM values of all 28 subjects were assessed by a linear regression, represented by the non-dashed line; the following results were obtained: $y=0.8876x+10.338$ and $r^2=0.3805$. The findings for the 28 subjects were found to be consistent with the state-of-the-art knowledge, showing that 80-90% of healthy people express DNIC under similar conditions, i.e. susceptive for an efficient CPM therapy. All subjects represented by the points to the right of the Y-axis are those that express a positive CPM value for a CS of 44.5° C., mostly perceived at sub-threshold levels. CPM values of the 13 subjects, at the $1^{st}$ quadrant, were assessed by a linear regression, represented by the dashed line; the following results were obtained: $y=0.9277x+9.2657$ and $r^2=0.4436$. This exhibits that about 50% of subjects enrolled in the study express a positive CPM value for a non-painful stimuli, e.g. sub-threshold levels, to an extent proportional to that induced by painful stimuli.

It will be appreciated that the present invention is not limited by what has been particularly described and shown hereinabove and that numerous modifications, all of which fall within the scope of the present invention, exist. Rather the scope of the invention is defined by the claims which follow:

The invention claimed is:

1. A method of conducing a conditioning modulation of pain perception (CPM), said method comprises: [a] identifying a patient; [b] determining the CPM profile of said patient, comprising: [i] subjecting said patient to a conditioning stimulus (CS); [ii] subjecting said patient to a test stimuli (TS), jointly and severally to said conditioning stimulus (CS), and [iii] rating the intensities of pain sensations evoked by said TS, respectively with and without said CS; and [iv] evaluating the difference between said ratings obtained with and without said CS; thereby assessing the susceptibility of said patient to CPM therapy; [c] selecting at least one site suitable for the delivery of a therapeutic CPM stimulation; wherein said selection is performed in accordance with the Diffuse Noxious Inhibitory Control (DNIC) paradigm; [d] applying said therapeutic CPM stimulation to at least one said suitable site; thereby conducing the conditioning modulation of pain perception (CPM) by said subject, wherein said selecting at least one location suitable for the delivery of a therapeutic CPM stimulation comprises: i. diagnosing said patient for a non-localized pain; ii. Arbitrarily selecting at least one dermatome; iii. Applying a therapeutic CPM stimulation to said dermatome; iv. Empirically evaluating the conduced CPM effect; v. preselecting, in accordance with said DNIC paradigm and based upon said empirical evaluation, a plurality of dermatomes, application of stimulation to which is putatively to conduce a CPM effect; and vi. Selecting from said plurality of preselected dermatomes at least one dermatome overlaying a site that physically/anatomically facilitates an efficient application of said CPM stimulation and/or implantation of an electrical electrode therefore.

\* \* \* \* \*